(12) United States Patent
Deschamps et al.

(10) Patent No.: US 8,314,232 B2
(45) Date of Patent: Nov. 20, 2012

(54) PREPARATION OF A QUINOLINYLOXYDIPHENYL CYCLOPROPANEDICARBOXAMIDE

(75) Inventors: Nicole Marie Deschamps, Research Triangle Park, NC (US); Michael Tolar Martin, Research Triangle Park, NC (US); Michael John Monteith, Research Triangle Park, NC (US); Xiaoming Zhou, Research Triangle Park, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 377 days.

(21) Appl. No.: 12/566,707

(22) Filed: Sep. 25, 2009

(65) Prior Publication Data

US 2010/0081805 A1    Apr. 1, 2010

Related U.S. Application Data

(60) Provisional application No. 61/100,452, filed on Sep. 26, 2008.

(51) Int. Cl.
*C07D 413/12* (2006.01)
(52) U.S. Cl. ....................................................... 544/128
(58) Field of Classification Search ................... 544/128
See application file for complete search history.

(56) References Cited

FOREIGN PATENT DOCUMENTS

| WO | WO 2005/030140 | * | 4/2005 |
|----|----------------|---|--------|
| WO | WO 2005/030140 A2 | | 4/2005 |
| WO | WO 2005/073224 A2 | | 8/2005 |

OTHER PUBLICATIONS

Harmange, et al., "Naphthamides as Novel and Potent Vascular Endothelial Growth Factor Receptor Tyrosine Kinase Inhibitors: Design, Synthesis, and Evaluation", *Journal of Medicinal Chemistry*, 2008, vol. 51, No. 6, pp. 1649-1667.

Burgos, et al., "Significantly improved method for the Pd-catalyzed coupling of phenols with aryl halide: understanding ligand effects", *Angewandte Chemie.*, 2006, vol. 45, pp. 4321-4326.

D'Angelo, et al, "Design, Synthesis, and Biological Evaluation of Potent c-Met", *Journal of Medicinal Chemistry*, 2008, vol. 51, No. 18, pp. 5766-5779.

* cited by examiner

*Primary Examiner* — Rebecca Anderson
(74) *Attorney, Agent, or Firm* — Andrea V. Lockenour; Edward R. Gimmi

(57) ABSTRACT

The present invention relates to a process of preparing a compound of the following formula III:

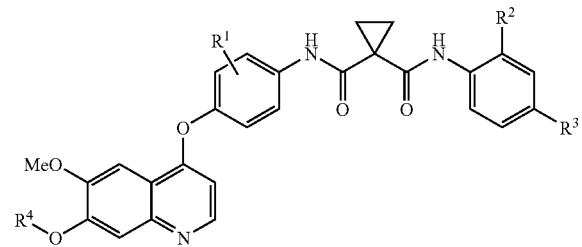

III wherein $R^1$-$R^4$ are as defined herein. The present invention also relates to the preparation of intermediates used to prepare the compound of formula III.

11 Claims, No Drawings

PREPARATION OF A QUINOLINYLOXYDIPHENYL CYCLOPROPANEDICARBOXAMIDE

CROSS REFERENCE TO PRIOR APPLICATIONS

This application claims the benefit of U.S. Provisional 61/100,452 filed 26 Sep. 2008.

BACKGROUND OF THE INVENTION

The development of small-molecule drugs that inhibit cell proliferation and angiogenesis (two key cellular processes needed for tumor growth) is prevalent. A particularly attractive target for small-molecule inhibition is the kinase c-Met, expression of which occurs in a wide variety of cell types where activation of the receptor induces cell migration, invasion, proliferation, and other biological activities associated with invasive cell growth. As such, signal transduction through c-Met receptor activation is responsible for many of the characteristics of tumor cells. Accordingly, the discovery of small-molecule inhibitors of c-Met is an ongoing challenge to the researcher.

Substituted quinolines have been reported to be promising for c-Met inhibition. For example, WO2005/030140 discloses a series of quinolinyloxydiphenylcyclopropanedicarboxamides, including $N^1$-{3-fluoro-4-[(6-(methyloxy)-7-{[3-(4-morpholinyl)propyl]oxy}-4-quinolinyl)oxy]phenyl}-$N^1$-(4-fluorophenyl)-1,1-cyclopropanedicarboxamide (illustrated), the preparation of which is described in Examples 25 (pp 193-194), 36 (pp 202-204), and 42-44 (pp 208-209) of the patent publication.

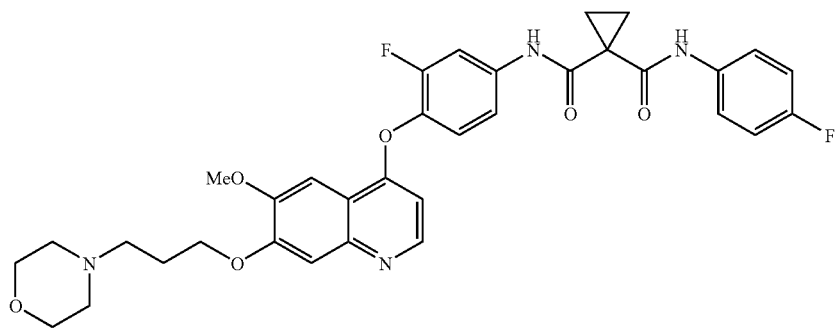

$N^1$-{3-fluoro-4-[(6-(methyloxy)-7-{[3-(4-morpholinyl)propyl]oxy}-4-quinolinyl)oxy]phenyl}-$N^1$-(4-fluorophenyl)-1,1-cyclopropanedicarboxamide The discovery of alternative synthetic routes to this purportedly potent class of c-Met inhibitors is highly desirable.

SUMMARY OF THE INVENTION

In one embodiment, the present invention relates to a method comprising contacting a compound of formula I:

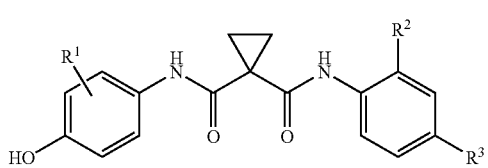

with a compound of formula II:

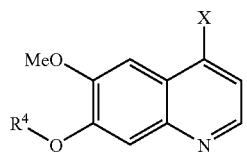

under such conditions to form a compound of formula III:

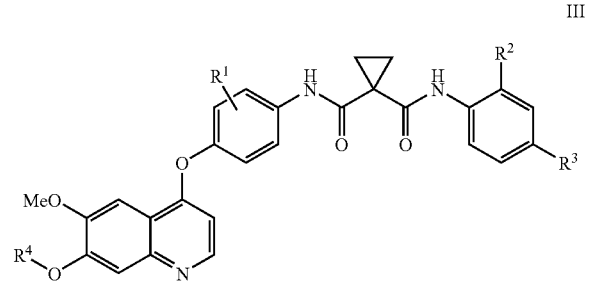

where X is a leaving group;
$R^1$, $R^2$, and $R^3$ are each independently H, F, or Cl;
$R^4$ is methyl or

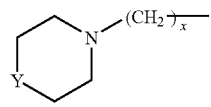

where Y is $CH_2$, O, NH, or N—$CH_3$; and
x is 2, 3, or 4.

In a second embodiment, the present invention relates to a method comprising:
a) reducing 2-fluoro-4-nitrophenol to form 4-amino-2-fluorophenol;
b) contacting 1-{[(4-fluorophenyl)amino]carbonyl}cyclopropanecarbonyl chloride with 4-amino-2-fluorophenol in the presence of a base to form $N^1$-(3-fluoro-4-hydroxyphenyl)-$N^1$-(4-fluorophenyl)-1,1-cyclopropanedicarboxamide; and
c) contacting $N^1$-(3-fluoro-4-hydroxyphenyl)-$N^1$-(4-fluorophenyl)-1,1-cyclopropanedicarboxamide with a compound of formula IIa:

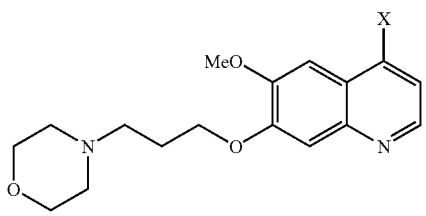

under such conditions to form $N^1$-{3-fluoro-4-[(6-(methyloxy)-7-{[3-(4-morpholinyl)propyl]oxy}-4-quinolinyl)oxy]phenyl}-$N^1$-(4-fluorophenyl)-1,1-cyclopropanedicarboxamide;

wherein X is a leaving group.

In a third embodiment, the present invention relates to a method comprising the steps of:
a) contacting 1,3,2-dioxathiane 2,2-dioxide with 4-hydroxy-3-methoxyacetophenone to form 3-{[4-acetyl-2-(methyloxy)phenyl]oxy}propyl hydrogen sulfate;
b) contacting 3-{[4-acetyl-2-(methyloxy)phenyl]oxy}propyl hydrogen sulfate with morpholine in the presence of a base and a phase transfer reagent to form 1-(3-(methyloxy)-4-{[3-(4-morpholinyl)propyl]oxy})acetophenone;
c) nitrating 1-(3-(methyloxy)-4-{[3-(4-morpholinyl)propyl]oxy})acetophenone to form 1-(5-(methyloxy)-4-{[3-(4-morpholinyl)propyl]oxy}-2-nitro)acetophenone;
d) reducing 1-(5-(methyloxy)-4-{[3-(4-morpholinyl)propyl]oxy}-2-nitro)acetophenone under such conditions to form 1-(2-amino-5-(methyloxy)-4-{[3-(4-morpholinyl)propyl]oxy})acetophenone; and
e) contacting 1-(2-amino-5-(methyloxy)-4-{[3-(4-morpholinyl)propyl]oxy})acetophenone with oxalyl chloride and methyl(phenyl)formamide or DMF or a combination thereof under such conditions to form 4-chloro-6-(methyloxy)-7-{[3-(4-morpholinyl)propyl]oxy}quinoline.

In a fourth embodiment, the present invention is a method comprising contacting a 2-aminoacetophenone with oxalyl chloride and a formamide under such conditions to form a 4-chloroquinoline.

In a fifth embodiment, the present invention is a compound having the following formula:

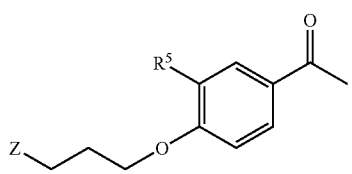

where Z is —$N(R^6)_2$, —$OSO_3H$, or —$OSO_3^-$ $M^+$;
$R^5$ is H, OH, $C_1$-$C_6$-alkyl, or $C_1$-$C_6$-alkoxy;
each $R^6$ is independently H, $C_1$-$C_6$-alkyl or, together with the nitrogen atom to which they are attached, form a piperidinyl, piperazinyl, N-methyl-piperazinyl, or morpholino group; and
M is Li, Na, or potassium.

DETAILED DESCRIPTION OF THE INVENTION

In one embodiment, the present invention relates to a method comprising contacting a compound of formula I:

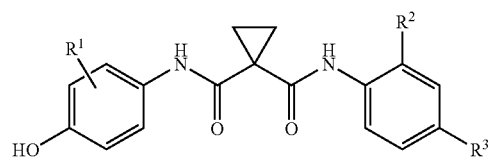

with a compound of formula II:

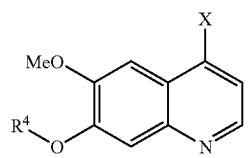

under such conditions to form a compound of formula III:

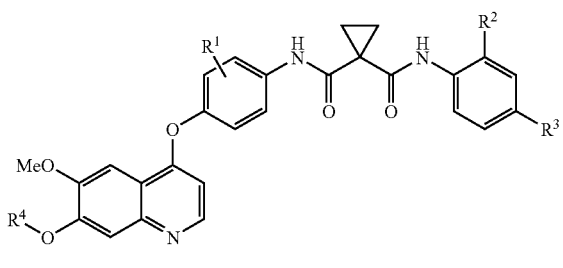

where X is a leaving group;
$R^1$, $R^2$, and $R^3$ are each independently H, F, or Cl;
$R^4$ is methyl or

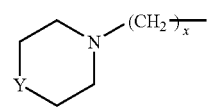

where Y is $CH_2$, O, NH, or N—$CH_3$; and
x is 2, 3, or 4.

Examples of leaving group X include F, Cl, Br, triflate, and tosylate.

$R^1$, $R^2$, and $R^3$ are preferably either F or H; Y is preferably O; and x is preferably 3.

$R^1$ is preferably ortho to the quinolinoxy group as illustrated:

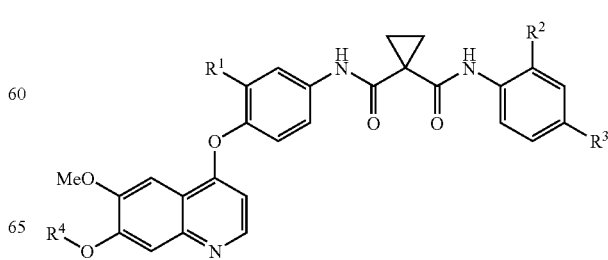

Preferably, $R^1$ and $R^3$ are each F; $R^2$ is preferably H; and $R^4$ is preferably:

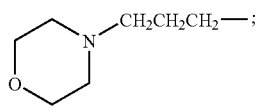

The compound of formula I is advantageously prepared by contacting under appropriate conditions a compound of formula IV:

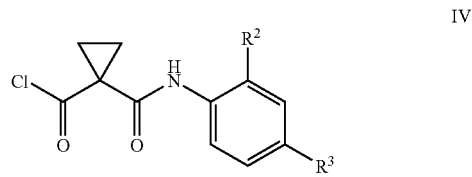

with a p-aminophenol of formula V:

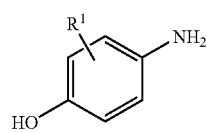

where $R^1$, $R^2$, and $R^3$ are as previously defined.

The compound of formula IV can be prepared in accordance with the following scheme:

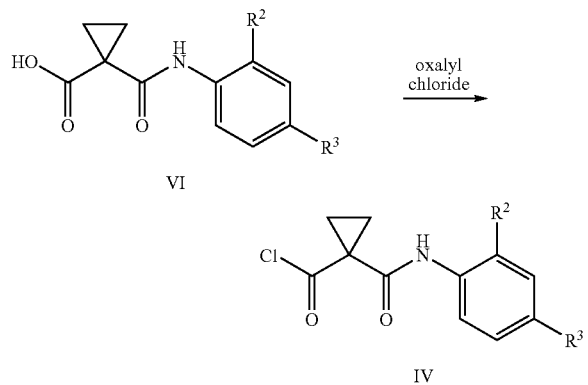

Thus, the compound of formula I can be prepared as follows: Oxalyl chloride is advantageously added slowly to the compound of formula VI in the presence of a suitable solvent and a catalytic amount of DMF and at a reduced temperature, typically from about 0° C. to about 20° C. to form the corresponding acid chloride of formula IV. The acid chloride is advantageously added slowly to a chilled solution containing the 4-aminophenol of formula V, typically from about 0° C. to about −20° C., to form the compound of formula I.

The 4-aminophenol of formula V can be prepared by the reduction of the corresponding 4-nitrophenol VII in the presence of a suitable solvent, catalyst, and hydrogenating agent.

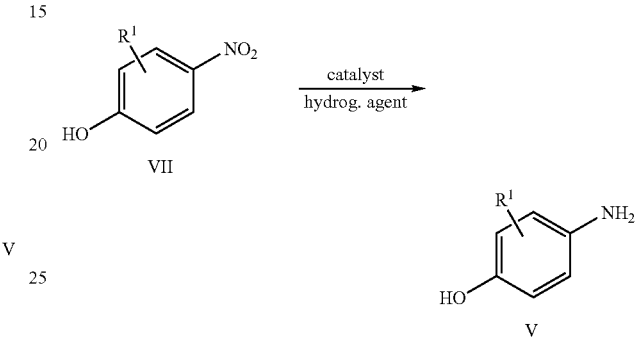

Examples of suitable catalysts include Pt and Pd, such as 10% Pd/C or 1% Pt/2% V. Examples of suitable hydrogenating agents include formic acid or formate salts, alone or in combination, preferably in combination, or hydrogen. Examples of formate salts include potassium formate, sodium formate, ammonium formate, triethylammonium and formate.). The reaction is advantageously carried out in a polar solvent such as THF, water or ethanol, or a combination of water and ethanol.

Examples of suitable solvents used in the preparation of the acid chloride of formula IV are quite extensive, and include THF, 2-butanone, toluene, 1,1,1,-trifluorotoluene, $CH_2Cl_2$, and acetone. Moreover, catalytic amounts of DMF are advantageously included in this reaction. Examples of suitable solvents used in the preparation of the compound of formula I include polar aprotic solvents such as NMP, DMF, dimethylacetamide.

The compound of formula I is reacted with the compound of formula II under suitable conditions to form the compound of formula III.

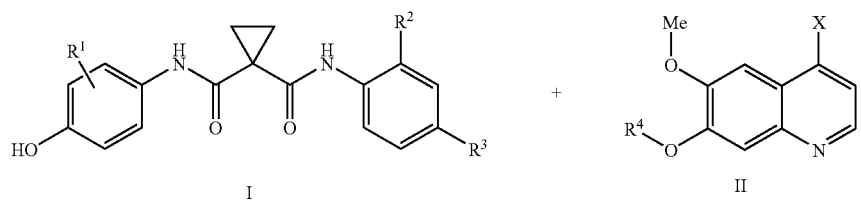

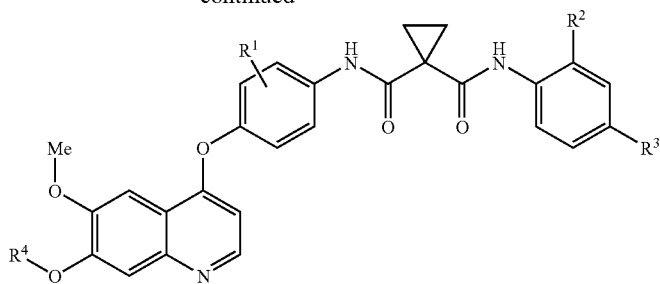

III

The displacement reaction is advantageously carried out in a suitable solvent in the presence of a base and a catalyst. Examples of suitable solvents include toluene, anisole, diethyl carbonate, N-methylpyrrolidone, and 1,3-dimethyl-3,4,5,6-tetrahydro-2(1H)-pyrimidinone, and combinations thereof. Examples of suitable bases include $Na_2CO_3$, $K_2CO_3$, $K_3PO_4$, and potassium tert-butoxide. A particularly suitable catalyst is a Pd catalyst such as $Pd(OAc)_2$ advantageously in combination with a ligand such as a phosphine ligand catalyst. Examples of suitable phosphine ligand catalysts include 1'-(di-tert-butylphosphino)-1,2,3,4,5-pentaphenylferrocene; 1,2,3,4,5-pentaphenyl-1'-(di-tert-butylphosphino)ferrocene; 2-di-tert-butylphosphino-2'-(N,N-dimethylamino)biphenyl; di-tent-butyl(2',4',6'-triisopropylbiphenyl-2-yl)phosphine; racemic 2-[di(tert-butyl)phosphino]-1,1'-binaphthyl; 2-di-tert-butylphosphino-3,4,5,6-tetramethyl-2',4',6'-triisopropyl-1,1'-biphenyl; 2-(di-tent-butylphosphino)-1-phenylindole; N-2-methoxyphenyl-2-di-tert-butylphosphino pyrrole; 1-phenyl-2-(di-tert-butyl-phosphino)-1H-pyrrole; 2-(di-t-butylphosphino)-2'-methylbiphenyl; 2-(di-tert-butylphosphino)biphenyl; and mixtures thereof; an example of a suitable mixture is 9,9-dimethyl-4,5-bis(diphenylphosphino)xanthene and di-tert-butyl(2',4',6'-triisopropylbiphenyl-2-yl) phosphine.

Examples of the compound of formula I include: $N^1$-(2,4-difluorophenyl)-$N^1$-(3-fluoro-4-hydroxyphenyl)-1,1-cyclopropanedicarboxamide; $N^1$-(3-fluoro-4-hydroxyphenyl)-$N^1$-(4-fluorophenyl)-1,1-cyclopropanedicarboxamide; $N^1$-(4-fluorophenyl)-$N^1$-(4-hydroxyphenyl)-1,1-cyclopropanedicarboxamide; $N^1$-(2-fluorophenyl)-$N^1$-(4-hydroxyphenyl)-1,1-cyclopropanedicarboxamide; $N^1$-(4-chloro-2-fluorophenyl)-$N^1$-(4-hydroxyphenyl)-1,1-cyclopropanedicarboxamide; $N^1$-(2-chloro-4-fluorophenyl)-$N^1$-(4-hydroxyphenyl)-1,1-cyclopropanedicarboxamide; $N^1$-(2,4-dichlorophenyl)-$N^1$-(4-hydroxyphenyl)-1,1-cyclopropanedicarboxamide; with $N^1$-(3-fluoro-4-hydroxyphenyl)-$N^1$-(4-fluorophenyl)-1,1-cyclopropanedicarboxamide (illustrated) being preferred.

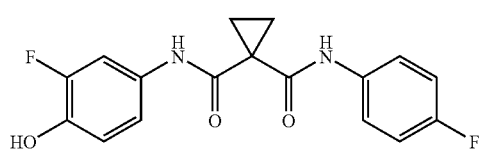

$N^1$-(3-fluoro-4-hydroxyphenyl)-$N^1$-(4-fluorophenyl)-1,1-cyclopropanedicarboxamide Examples of the compound of formula II include: 4-chloro-6,7-bis(methyloxy)quinoline; 4-chloro-6-(methyloxy)-7-{[3-(4-morpholinyl)propyl]oxy}quinoline; 4-chloro-6-(methyloxy)-7-{[3-(1-piperazinyl)propyl]oxy}quinoline; and 4-chloro-6-(methyloxy)-7-{[3-(4-methyl-1-piperazinyl)propyl]oxy}quinoline; with 4-chloro-6-(methyloxy)-7-{[3-(4-morpholinyl)propyl]oxy}quinoline (illustrated) being preferred.

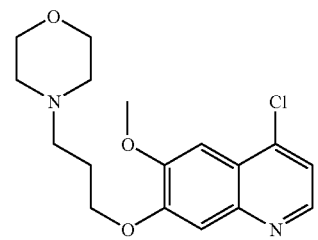

4-chloro-6-(methyloxy)-7-{[3-(4-morpholinyl)propyl]oxy}quinoline

An especially preferred example of the compound of formula III is $N^1$-{3-fluoro-4-[(6-(methyloxy)-7-{[3-(4-morpholinyl)propyl]oxy}-4-quinolinyl)oxy]phenyl}-$N^1$-(4-fluorophenyl)-1,1-cyclopropanedicarboxamide:

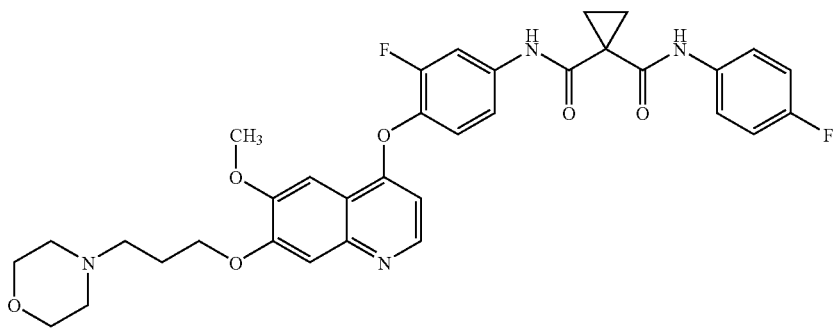

N[1]-{3-fluoro-4-[(6-(methyloxy)-7-{[3-(4-morpholinyl)propyl]oxy}-4-quinolinyl)oxy]phenyl}-N[1]-(4-fluorophenyl)-1,1-cyclopropanedicarboxamide Examples of the compound of formula IV include 1-{[(2,4-difluorophenyl)amino]carbonyl}cyclopropanecarbonyl chloride; 1-{[(4-fluorophenyl)amino]carbonyl}cyclopropanecarbonyl chloride; 1-{[(2-fluorophenyl)amino]carbonyl}cyclopropanecarbonyl chloride; 1-{[(4-chloro-2-fluorophenyl)amino]carbonyl}cyclopropanecarbonyl chloride; 1-{[(2-chloro-4-fluorophenyl)amino]carbonyl}cyclopropanecarbonyl chloride; and 1-{[(2,4-dichlorophenyl)amino]carbonyl}cyclopropanecarbonyl chloride; with 1-{[(4-fluorophenyl)amino]carbonyl}cyclopropanecarbonyl chloride (illustrated) being preferred.

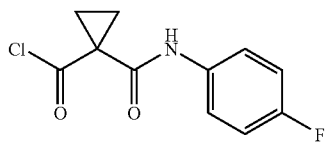

1-{[(4-fluorophenyl)amino]carbonyl}cyclopropanecarbonyl chloride

A preferred example of the compound of formula V is 4-amino-2-fluorophenol. Accordingly, the preferred compound of formula I is N[1]-(3-fluoro-4-hydroxyphenyl)-N[1]-(4-fluorophenyl)-1,1-cyclopropanedicarboxamide.

Schemes

The following steps illustrate the process of the present invention. Specific reagents referred to are also illustrative and not intended to be limiting. Compounds for which synthetic details are not provided are either commercially available or are readily prepared by one skilled in the art using available starting materials.

Scheme 1 summarizes the steps for the preparation of the compound of formula I.

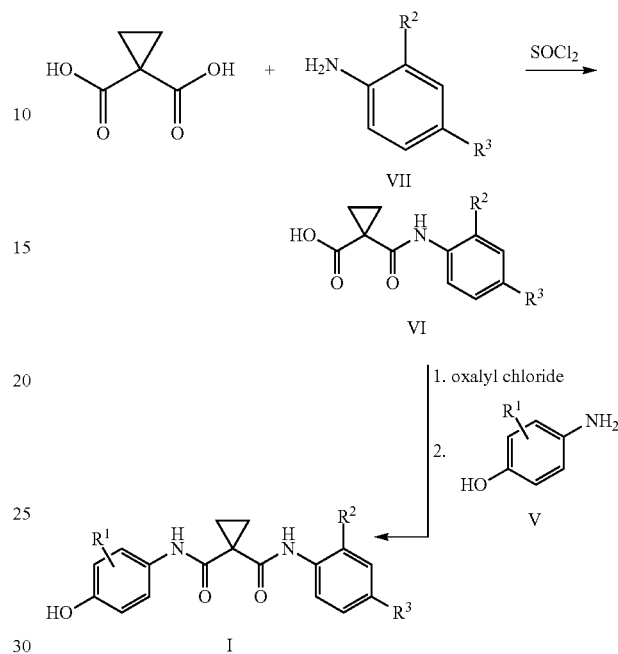

Scheme 1

1,1,-Cyclopropanedicarboxylic acid can be contacted with thionyl chloride, then the aniline (VIII) to form the acid (VI); the acid (VI) can then be contacted with oxalyl chloride, then the aminophenol (V) to form the N[1]-4-hydroxyphenyl-N[1]-phenyl-1,1-cyclopropanedicarboxamide (I).

Scheme 2 illustrates steps for the preparation of a preferred compound of formula II, 4-chloro-6-(methyloxy)-7-{[3-(4-morpholinyl)propyl]oxy}quinoline.

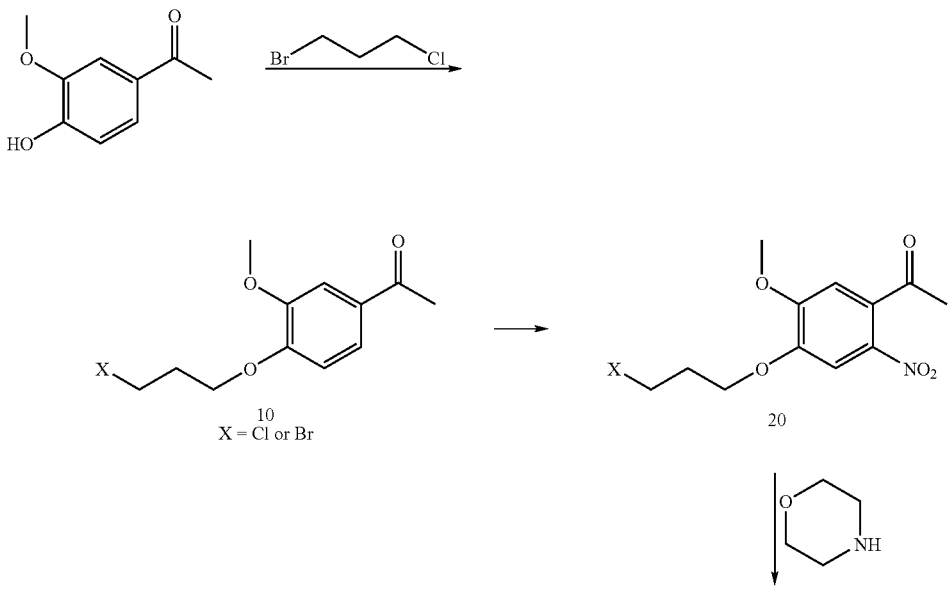

Scheme 2

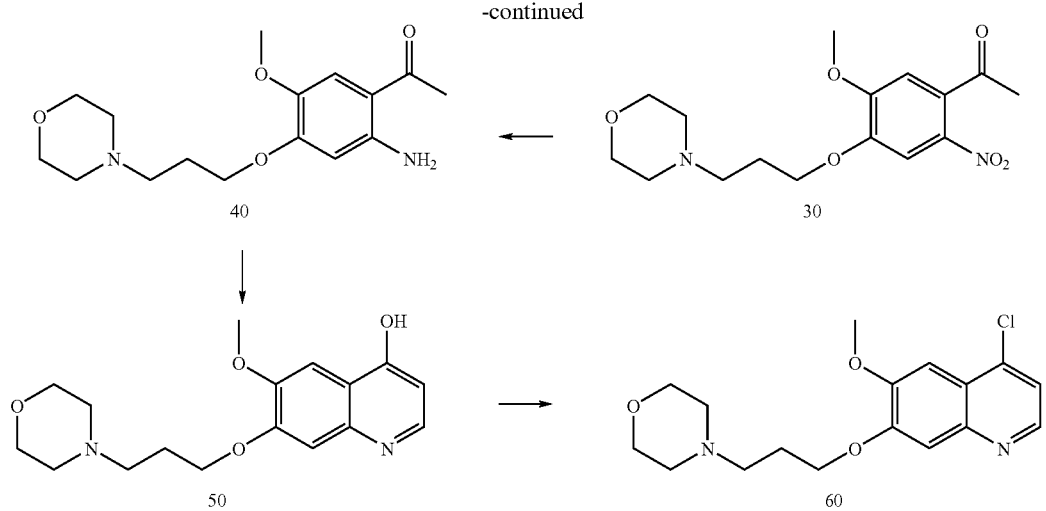

4-Hydroxy-3-methoxy-acetophenone can be contacted with 1-bromo-3-chloropropane in the presence of a suitable base such as potassium carbonate and a phase transfer reagent such as tetrabutylammonium bromide under such conditions to form a mixture of the halopropyloxymethyloxyphenyl-lacetophenones (10). This mixed halide can be nitrated with nitric acid and sulfuric acid to produce intermediate (20), which can be reacted with morpholine to form 1-(5-(methyloxy)-4-{[3-(4-morpholinyl)propyl]oxy}-2-nitro)acetophenone (30). Intermediate (30) can be reduced to the corresponding aniline (40) with, for example, formic acid and potassium formate and a catalytic amount of 10% Pd/C. Aniline (40) can be converted to the hydroxyquinoline (50) using a suitable base such as sodium ethoxide and an alkyl formate such as ethyl formate. Finally, the hydroxyquinoline (50) can be converted to the chloroquinoline (60) using a chlorinating agent such as POCl$_3$.

Scheme 3 illustrates the preparation of a subgenus of the compound of formula III where R$^4$ is a morpholino-n-propyl group.

Scheme 3

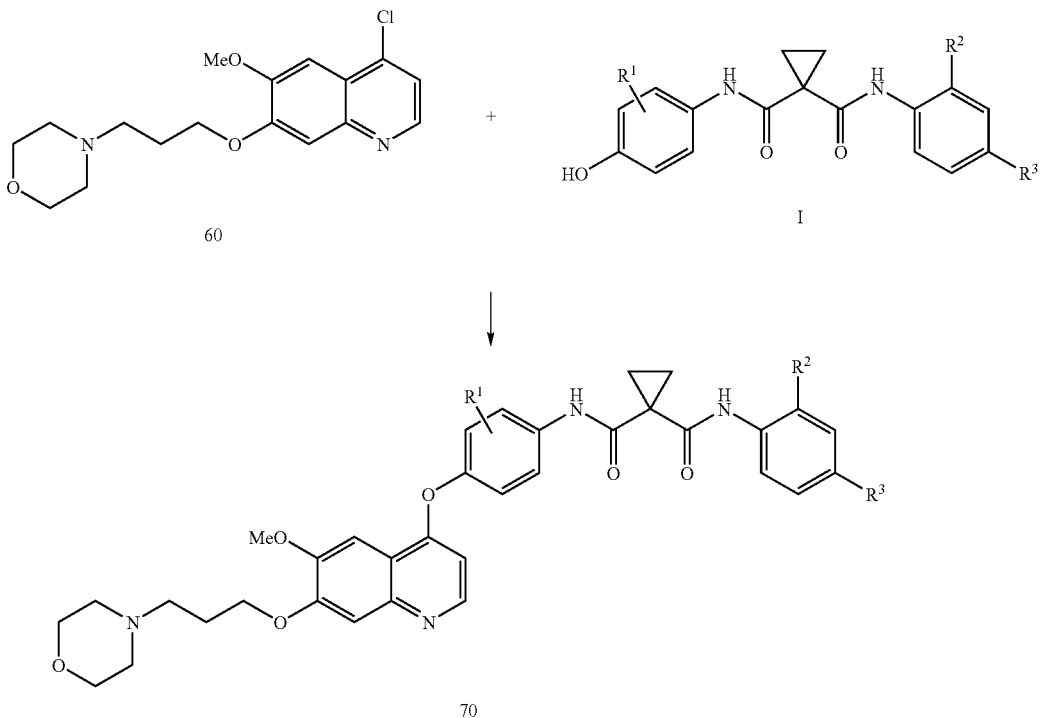

In the above scheme, the compound of formula (70) can be prepared by contacting chloroquinoline (60) with the compound of formula I in the presence of a base such as K$_3$PO$_4$, a metal catalyst such as Pd(OAc)$_2$, a phosphine ligand such as racemic-2-(di-tert-butylphosphino)-1,1'-binaphthyl, and in the presence of a suitable solvent such as toluene, NMP, 1,3-dimethyl-3,4,5,6-tetrahydro-2(1H)-pyrimidinone (DMPU), anisole, a mixture of toluene and NMP and a mixture of toluene and DMPU.

Scheme 4 represents the preparation of chloroquinoline (60) by an alternative route.

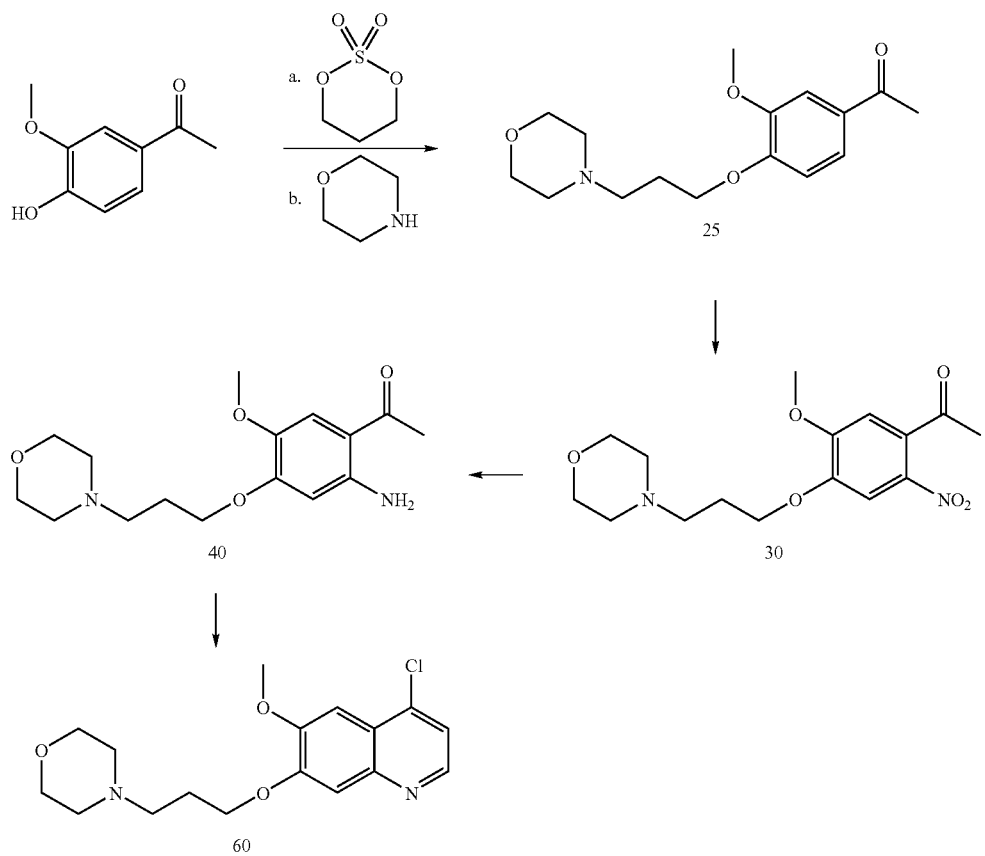

4-Hydroxy-3-methoxy-acetophenone can be contacted with 1,3,2-dioxathiane 2,2-dioxide then morpholine to form acetophenone (25). Acetophenone (25) can be nitrated to form the nitroacetophenone (30), which can be reduced to from the aminoacetophenone (40), which can be cyclized and chlorinated in one step to form the substituted quinoline (60) using a suitable chlorinating reagent, such as oxalyl chloride, and a suitable formamide, such as methyl(phenyl)formamide or DMF or a combination thereof.

The conversion of aniline (40) to chloroquinoline (60) is applicable for a wide variety of 2-aminoacetophenones. Thus, in another aspect, the present invention is a method comprising contacting a 2-aminoacetophenone with a suitable chlorinating reagent (for example, oxalyl chloride, thionyl chloride, or phosphorous oxychloride) and a suitable formamide; alternatively the 2-aminoacetophenone can be contacted with the product of a chlorinating reagent and a formamide (for example (chloromethylene)dimethylammoniumchloride (Vilsmeier reagent)) under such conditions to form a 4-chloroquinoline.

In another embodiment, the present invention is a compound represented by the following formula IX:

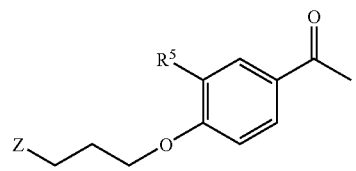

where Z is —N(R$^6$)$_2$ or —OSO$_2$-M;

R$^5$ is H, OH, C$_1$-C$_6$-alkyl, or C$_1$-C$_6$-alkoxy;

each R$^6$ is independently H, C$_1$-C$_6$-alkyl or, together with the nitrogen atom to which they are attached, form a piperidinyl, piperazinyl, N-methyl-piperazinyl, or morpholino group; and M is OH, O$^-$Li$^+$, O$^-$Na$^+$, or O$^-$K$^+$.

In another aspect, compound IX is represented by either of the following formulae:

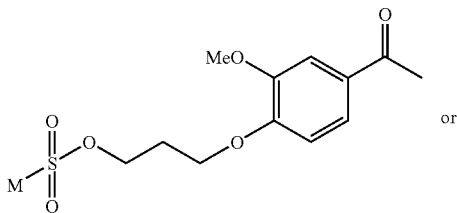

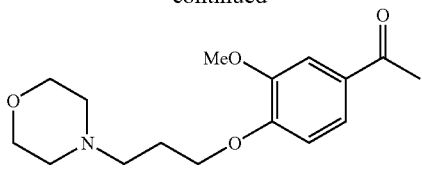

EXAMPLES

The experimental details for the process of the present are for illustrative purposes only and not intended to limit the manner in which the compounds are made.

1. Preparation of $N^1$-(3-Fluoro-4-hydroxyphenyl)-$N^1$-(4-fluorophenyl)-1,1-cyclopropanedicarboxamide

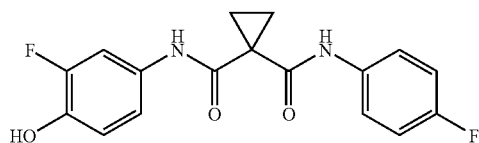

$N^1$-(3-Fluoro-4-hydroxyphenyl)-$N^1$-(4-fluorophenyl)-1,1-cyclopropanedicarboxamide A. 1-{[(4-Fluorophenyl)amino]carbonyl}cyclopropanecarboxylic Acid

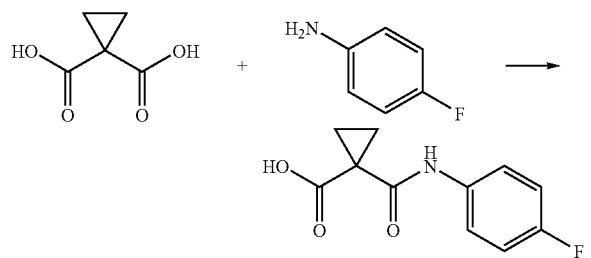

A reactor was charged with 1,1,-cyclopropanedicarboxylic acid (28.3 Kg, 218 mol) and tetrahydrofuran (177 Kg) and stirred with cooling to 5° C. The reactor was charged with triethylamine (22.0 Kg, 217 mol) at a rate to maintain reaction at <10° C.; the line was rinsed with 2 Kg of THF and stirring was continued at <10° C. for 30 min. The reactor was charged with thionyl chloride (25.9 Kg, 217 mol) and the line was rinsed with an additional 2 Kg of THF and stirring was continued at <10° C. for 2 h. The reactor was charged with a solution of 4-fluoroaniline (26.6 Kg, 239 mol) in THF (70.8 Kg) and allowed to stir at <10° C. for approximately 10 h. The reactor was then charged with isopropyl acetate (246 Kg) followed by a solution of 4 wt % NaOH in water (146 Kg) and stirred for 15 min. The lower aqueous layer was drained and the organic layer washed with water. The lower aqueous layer was drained again and the organic layer washed with a solution of 20 wt % sodium chloride (141.5 Kg). The aqueous layer was drained and the organic layer distilled in vacuo to approximately 110 L. The product was treated with heptane (192 Kg) and the contents were cooled and stirred at 20° C. for 3 h. The resulting solids were filtered and washed with heptane (113 Kg) to provide crude 1-{[(4-fluorophenyl)amino]carbonyl}cyclopropanecarboxylic acid (35.5 Kg). A glass column packed with 1 Kg sand was filled with 63-200 mesh silica gel (17 Kg) and methanol (80 Kg). The crude product was dissolved in methanol (283 Kg) and passed through the silica gel bed collecting the UV active eluent. Remaining product was flushed off the silica gel with additional methanol (25 Kg). The combined fractions were stirred in a vessel and treated with water (340 Kg); the contents were stirred at 20° C. for approximately 30 min.

The resulting solids were filtered and the product dried at 55° C. for 24 h to yield the product (30.6 Kg, 63%).

B. Preparation of $N^1$-(3-Fluoro-4-hydroxyphenyl)-$N^1$-(4-fluorophenyl)-1,1-cyclopropanedicarboxamide

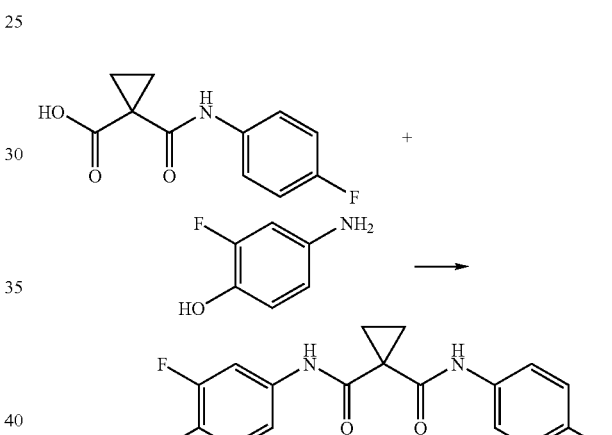

To a solution of 1-{[(4-fluorophenyl)amino]carbonyl}cyclopropanecarboxylic acid (21 g, 94.17 mmol) and DMF (0.11 mL) in THF (147 mL) was added oxalyl chloride (8.37 mL, 98.88 mmol) slowly to maintain a temperature in the range of 4° C. to 15° C. The solution was stirred at room temperature for about 2 h, then slowly added to a chilled (−10° C.) solution of 4-amino-2-fluoro phenol (14.05 g, 110.65 mmol) and 2,6-lutidine (21.90 mL) in THF (147 mL) over ~45 min. The temperature was maintained at or below 0° C. throughout the addition. The suspension was stirred for 0.5-1 h at 0° C. EtOAc (210 mL) and $H_2O$ (147 mL) were added and the layers were separated. 1N HCl (105 mL) was added to the organic portion and the layers separated. 5% $NaHCO_3$ (105 mL) was added to the organic portion and the layers separated. The solution was dried over $Na_2SO_4$ and concentrated to dryness. EtOAc (42 mL) was added to the residue and the resulting suspension was stirred at 55° C. for 1 h and cooled to 20° C. The suspension was stirred at room temperature overnight then cooled to 0-5° C. with stirring for 2-3 h. The solid was isolated by filtration and the cake was washed with 1:2 EtOAc/heptane (21 mL). The solid was dried under reduced pressure at 55° C. to give 28.43 g of the desired product (yield: 91%).

2. Preparation of 4-Chloro-6-(methyloxy)-7-{[3-(4-morpholinyl)propyl]oxy}quinoline

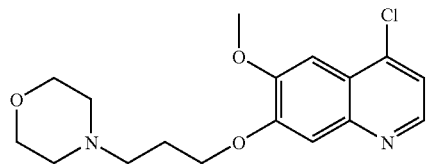

4-Chloro-6-(methyloxy)-7-{[3-(4-morpholinyl)propyl]oxy}quinoline

A. 1-[4-[(3-Halopropyl)oxy]-3-(methyloxy)]acetophenones

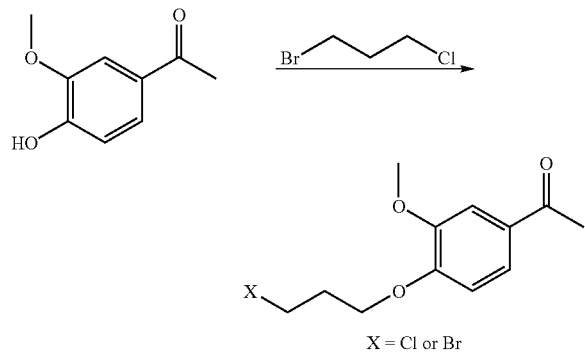

X = Cl or Br

A reactor was charged with water (300 Kg) and potassium carbonate (124.8 kg, 903 mol) and the contents stirred at 25° C. to dissolve. The reactor was then charged with 1-bromo-3-chloropropane (210 Kg, 1334 mol), tetrabutylammonium bromide (7.35 kg, 22.8 mol) and 4-hydroxy-3-methoxy-acetophenone (75.0 kg, 451 mol). The resulting biphasic mixture was heated to approximately 80° C. and maintained for approximately 90 min. The reaction mixture was cooled to 25° C. and agitation stopped. The organic layer was transferred to an adjacent reactor and the reaction mixture was charged with methylene chloride (198 Kg) and stirred for 15 minutes. After the stirring was stopped, the layers were allowed to settle. The methylene chloride layers were combined and the aqueous layer was discarded. The combined methylene chloride solution was washed with water and the solution containing the mixture of 1-[4-[(3-halopropyl)oxy]-3-(methyloxy)]acetophenones (where halo in this case is bromo and chloro) was used in the next step without further processing.

B. 1-[4-[(3-Halopropyl)oxy]-5-(methyloxy)-2-nitro]acetophenone

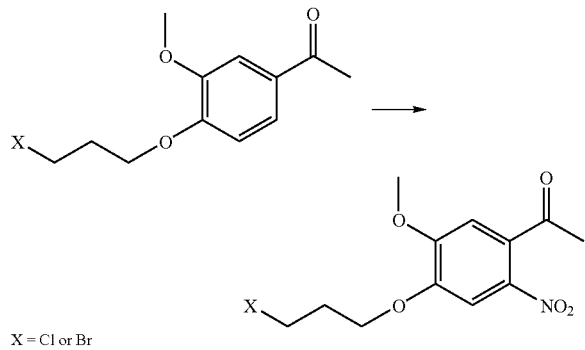

X = Cl or Br

Water (105 Kg) was charged to the solution of the 1-[4-[(3-halopropyl)oxy]-3-(methyloxy)]acetophenones from step A and the solution was cooled to ~4° C. Concentrated sulfuric acid (194.25 kg, 1980 mol) was added at a rate such that the batch temperature did not exceed ~18° C. The resulting solution was cooled to approximately 5° C., whereupon 70% nitric acid (113.7 kg, 1263 mol) was added at a rate such that the batch temperature did not exceed approximately ~10° C. The reaction mixture was allowed to stir at approximately 10° C. for approximately 1 h, then transferred with stirring to an adjacent reactor charged with methylene chloride (345 kg), water (187.5 kg), and ice (75.0 kg). After 15 minutes, the methylene chloride layer was separated and the aqueous layer washed with additional methylene chloride (150 kg). The organic portions were combined and washed with ~5% w/w aqueous potassium bicarbonate solution (2x~285 Kg), then water (210 Kg), then heated to approximately 60° C. and concentrated by vacuum distillation to a final volume of approximately 190 L. 1-Butanol (705 kg) was added and the mixture was again concentrated by vacuum distillation at 60° C. to a final volume of approximately 300 L. The resulting solution was stirred at approximately 20° C. during which time the product crystallized. The solids were collected by filtration, washed with heptane (127 Kg) and spun dry on centrifuge to afford the mixture of 1-[4-[(3-halopropyl)oxy]-5-(methyloxy)-2-nitro]acetophenones.

C. 1-(5-(Methyloxy)-4-{[3-(4-morpholinyl)propyl]oxy}-2-nitro)acetophenone

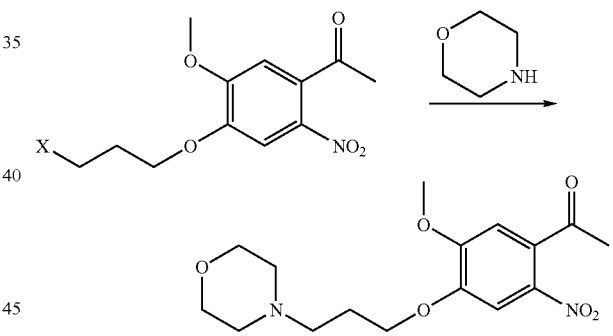

A reactor was charged with toluene (563 Kg) and the crude, solvent-wet solid mixture of 1-[4-[(3-halopropyl)oxy]-5-(methyloxy)-2-nitro]acetophenones from the previous step (130.6 Kg) was added with stirring to form a solution. A solution of potassium carbonate (94.5 Kg, 684 mol) and sodium iodide (48 Kg, 320 mol) in water (325 Kg) was charged into the reactor and the reaction was treated with tetrabutylammonium bromide (14.9 Kg, 46 mol) and morpholine (118.5 Kg, 1360 mol). The resulting 2-phase mixture was heated to ~85° C. for ~9 h after which time the mixture was cooled to 25° C. The organic layer was removed and the aqueous layer back extracted with toluene (150 Kg). The combined toluene layers were washed sequentially with two portions of a solution of sodium thiosulfate pentahydrate (27 Kg, 109 mol) in water (900 Kg) followed by two portions of water (450 Kg each). The reaction mixture was then distilled in vacuo at <60° C. to remove the toluene to ~⅓ the original volume (target 405 L). The solution containing the product was heated to approximately 50° C. and heptane (413 kg) was added. The reaction was cooled to 25° C. which resulted in the crystallization of the product. The product was centrifuged and washed with heptane (75 kg) and isolated as a solvent wet solid without oven drying (actual weight=128.3 kg). The dry mass was calculated as 97.3 Kg).

D. 1-(2-Amino-5-(methyloxy)-4-{[3-(4-morpholinyl)propyl]oxy})acetophenone

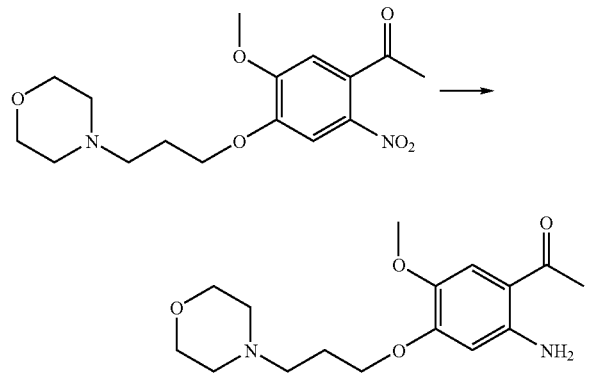

To the solvent wet solid from the previous step were added ethanol (574 Kg, 288 mol) and 10% Pd—C (50% water wet, 10.7 Kg). The resulting slurry was heated to approximately 50° C. and a solution of formic acid (40.9 Kg, 888 mol) and potassium formate (74.9 Kg, 890 mol) in water (97.3 Kg) was added via metering pump over 2 h. When the addition was complete and the reaction deemed complete by HPLC the contents were cooled to 25° C. and treated with water (600 Kg) to dissolve the by-product salts. The mixture was filtered to remove the insoluble catalyst and the filter rinsed with additional water (150 Kg). The filtrate was concentrated under reduced pressure and at <60° C. to collect a 750-L distillate. The contents were cooled to 25° C. and treated with toluene (260.0 Kg). The mixture was washed with a solution of potassium carbonate (45 Kg) in water (180 Kg) for thirty minutes. The pH was checked to determine it was >10. The toluene layer was separated and the aqueous layer was back extracted with toluene (312 Kg). The combined toluene phases were dried over anhydrous sodium sulfate (68 Kg). The drying agent was removed by filtration and washed with toluene (45 Kg). The solution was used as is for the following step.

E. 6-(Methyloxy)-7-{[3-(4-morpholinyl)propyl]oxy}-4-quinolinol

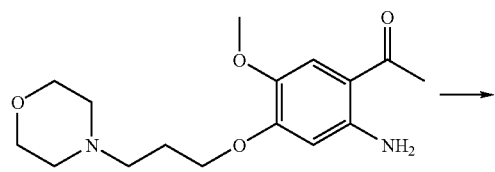

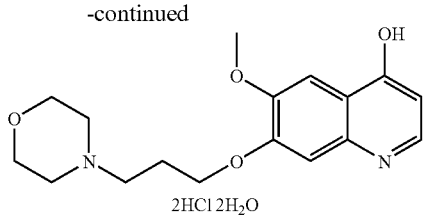

2HCl 2H₂O

A reactor was charged with ethanol (155.2 Kg) and cooled to 15° C. Sodium ethoxide (41.3 Kg, 607 mol was added at a rate to maintain a temperature of <20° C. Toluene (66.5 Kg) was added and sodium ethoxide/ethanol/toluene solution was added to the 1-(2-amino-5-(methyloxy)-4-{[3-(4-morpholinyl)propyl]oxy})acetophenone solution from the previous step (assumed 88.7 Kg, 288 mol) at a rate to maintain the temperature between 15 and 25° C. The reaction was allowed to stir for ~45 min then treated with ethyl formate (138.4 Kg, 1868 mol). The mixture was warmed to approximately 40° C. for about 3 h and monitored for completeness by HPLC. The reaction mixture was cooled to approximately 25° C. after deemed complete. The contents were cooled to 15-25° C. and treated with water (288 Kg). The pH of the solution was adjusted to below 2 by the addition of hydrochloric acid (37%, ~120 Kg). The organic and aqueous phases were separated and acetone (4.3 wt, 381 Kg) was added to the aqueous phase. The mixture was allowed to stir for approximately 5 h, by which time the product precipitated. The product was collected by filtration, and the cake was washed with acetone (102.6 Kg) and dried under reduced pressure at approximately 40° C. to afford 6-(methyloxy)-7-{[3-(4-morpholinyl)propyl]oxy}-4-quinolinol as the dihydrochloride dihydrate, which was shown to be 99% pure by HPLC and contained 0.3% by weight inorganic material (residue on ignition).

F. 4-Chloro-6-(methyloxy)-7-{[3-(4-morpholinyl)propyl]oxy}quinoline

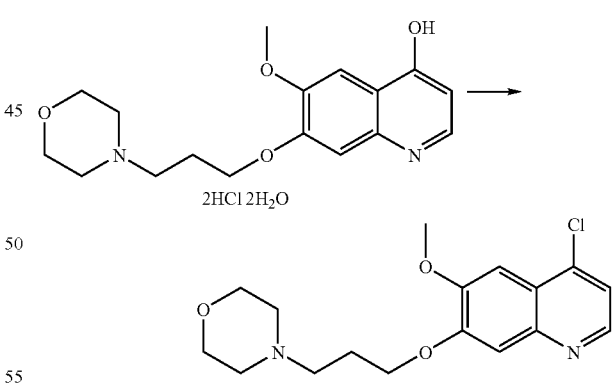

A reactor vessel was charged with the hydroxyquinoline dihydrochloride dihydrate (62.3 Kg, 159 mol) and acetonitrile (230 Kg) and the contents were stirred with heating to 45-55° C. A solution of POCl₃ (72.8 Kg, 475 mol) in acetonitrile (39 Kg) was prepared in a separate vessel and stirred for 15 minutes, then added to the reactor vessel while maintaining the temperature at 50-80° C. The vessel containing residual POCl₃ was rinsed with additional acetonitrile (25 Kg) and this solution was added to the reactor vessel. The reaction mixture was heated at reflux (82° C.) for 8 h at which time the reaction was deemed complete by HPLC analysis (<0.5% of hydroxyquinoline remaining). The reaction mixture was cooled to 15-25° C. and treated with toluene (150 Kg) followed by slow addition of a solution of KOH (127 Kg) in water (380 L) to achieve pH of 11 while maintaining the temperature to <25° C. The contents of the reactor were allowed to settle and the lower aqueous layer removed. The toluene phase was washed with water (63 L) and the lower aqueous layer drained. The reaction was distilled in vacuo to 5 volumes (316 L). Heptanes (215 L) were added and the mixture was distilled in vacuo to a final of 5 volumes (316 L), generating a free flowing precipitate. Heptanes (215 L) were added again and the mixture was distilled in vacuo to a final of 5 volumes (316 L). The reaction was then charged with heptanes (216 L) and the contents were cooled to 0-10° C. and allowed to stir for 1 h. The solids were filtered and the cake washed with heptane (75 Kg). The solid was dried on filter dryer at 30-35° C. for 8 h to afford 4-chloro-6-(methyloxy)-7-{[3-(4-morpholinyl)propyl]oxy}quinoline. 70% yield.

2A. Alternative preparation of 4-Chloro-6-(methyloxy)-7-{[3-(4-morpholinyl)propyl]oxy}quinoline A. 1-(5-(Methyloxy)-4-{[3-(4-morpholinyl)propyl]oxy})acetophenone from 4-Hydroxy-3-methoxy-acetophenone

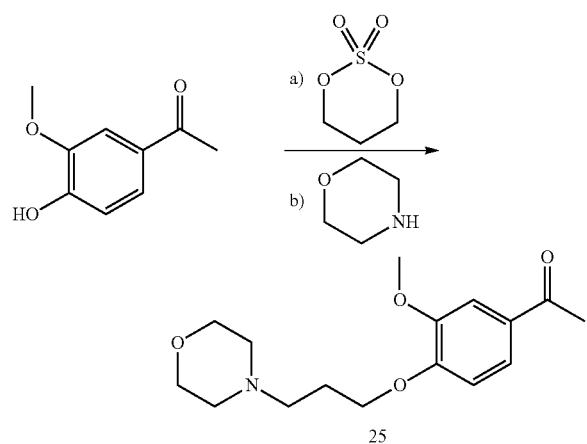

A reaction flask charged with 4-hydroxy-3-methoxyacetophenone (50 g, 0.3 mol), THF (500 mL), LiOH (21.6 g, 0.9 mol), and water (27 g, 1.5 mol) was heated to reflux with stirring. After 30 min, 1,3,2-dioxathiane 2,2-dioxide (52 g, 0.38 mol) was added and heating was continued for ~3 h. The reaction was distilled to a final volume of 25 mL. Morpholine (250 mL) was added and distillation was continued to a final volume of ~250 mL. Additional morpholine (100 mL) was charged into the reactor and heating at reflux was continued for ~3 h. The reaction mixture was cooled to ambient temperature and diluted with water and methylene chloride. The layers were separated and the aqueous layer was washed twice with additional methylene chloride. The combined organic layers were washed with brine after which most of the organic solvent was removed. Isopropyl acetate (150 mL) was added and distillation was continued to remove ~50 mL of residual methylene chloride. Heptane (150 mL) was then added and the contents were cooled to room temperature with seeding, which resulted in crystallization. After ~16 h of stirring, the contents were diluted with additional heptane (100 mL) and the solids filtered. The solids were washed with additional heptane and dried to give 1-(3-(methyloxy)-4-{[3-(4-morpholinyl)propyl]oxy})acetophenone. Yield: 49.3 g, 56%.

B. Preparation of 1-(5-(methyloxy)-4-{[3-(4-morpholinyl)propyl]oxy}-2-nitro)acetophenone

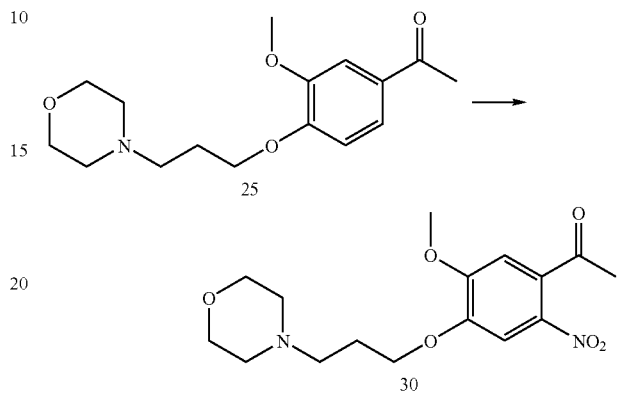

1-(3-(methyloxy)-4-{[3-(4-morpholinyl)propyl]oxy})acetophenone (25 g, 85.2 mmol) was charged into a reactor along with methylene chloride (100 mL) with stirring, then trifluoroacetic acid (62.5 mL) was added over 5 min. The solution was maintained at 20° C. and treated with 70% nitric acid (27.4 mL. 425 mmol). The reaction mixture was cooled and allowed to stir at ~10° C. for 45 min. Water (100 mL) was added and the pH adjusted to 11 by slow addition of 50% NaOH while maintaining temperature ~25-30° C. The product mixture was washed with methylene chloride (3×3 vol) and the organic solution was isolated and distilled to minimum volume, then and treated with ethanol (200 mL). The distillation continued to minimum volume and mixture was charged with ethanol (150 mL). The distillation continued to a final volume of 150 mL and the reactor was then charged with water (200 mL). The pH was adjusted to ~12 with NaOH, and the contents allowed to cool to 10° C. for 1 h. Solids were filtered and washed with water (2×2 vol) and dried to give intermediate (30) (20.2 g, 70% yield).

C. Preparation of 4-chloro-6-(methyloxy)-7-{[3-(4-morpholinyl)propyl]oxy}quinoline

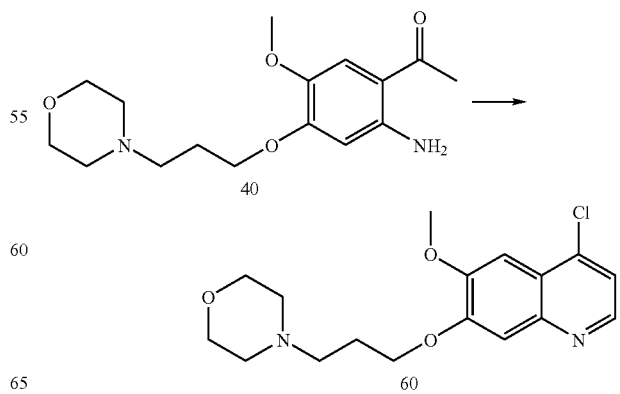

The aniline (40) can be prepared as shown in Step 2D. Methyl(phenyl)formamide (2.2 g, 16.3 mmol) was dissolved in dichloroethane (15 mL) and treated with oxalyl chloride (2.1 g, 16.5 mmol) and the solution was warmed to 45° C. for ~15 minutes at which time aniline (40) (1.0 g, 3.24 mmol) dissolved in dichloroethane (2 mL) was added. The reaction mixture was stirred at 60° C. for ~4 h after which time water (20 mL) was added. The aqueous layer was removed and washed with additional dichloroethane (20 mL). The pH of the aqueous layer was adjusted to ~12 by addition of NaOH and the aqueous layer was washed with methylene chloride (2×20 mL portions). The combined methylene chloride extracts were evaporated to an oil that was triturated in water to produce solids. The solids were filtered and dried to provide the 4-chloro-6-(methyloxy)-7-{[3-(4-morpholinyl)propyl]oxy}quinoline as an off-white solid, 0.36 g, 33% yield.

3. Preparation of $N^1$-{3-fluoro-4-[(6-(methyloxy)-7-{[3-(4-morpholinyl)propyl]oxy}-4-quinolinyl)oxy]phenyl}-$N^1$-(4-fluorophenyl)-1,1-cyclopropanedicarboxamide

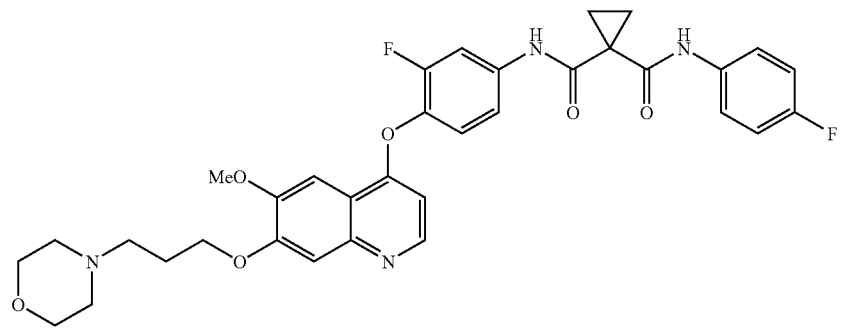

$N^1$-{3-fluoro-4-[(6-(methyloxy)-7-{[3-(4-morpholinyl)propyl]oxy}-4-quinolinyl)oxy]phenyl}-$N^1$-(4-fluorophenyl)-1,1-cyclopropanedicarboxamide

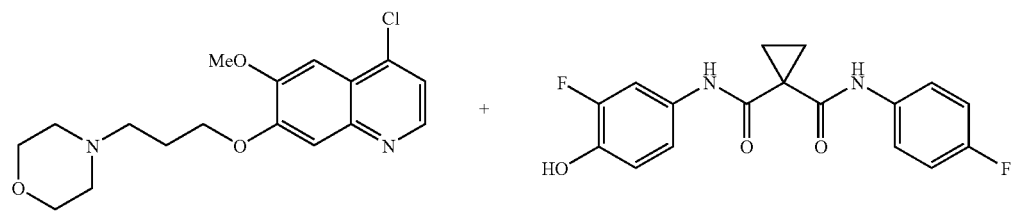

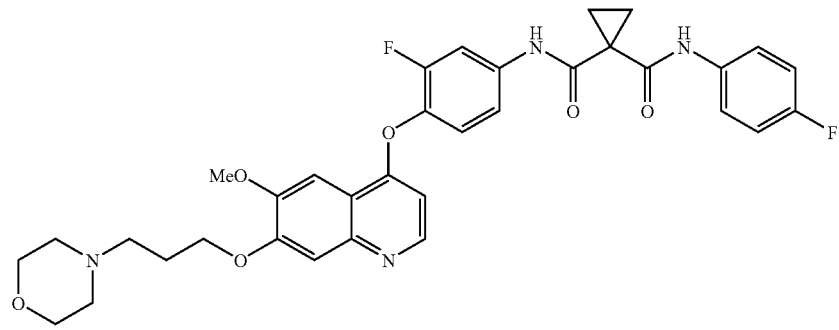

4-Chloro-6-(methyloxy)-7-{[3-(4-morpholinyl)propyl]oxy}quinoline (60 mg, 0.18 mmol), N¹-(3-Fluoro-4-hydroxyphenyl)-N¹-(4-fluorophenyl)-1,1-cyclopropanedicarboxamide, Pd(OAc)₂ (4 mg, 0.018 mmol), racemic-2-(di-tert-butylphosphino)-1,1'-binaphthyl (14.2 mg, 0.035 mmol), and K₃PO₄ (57 mg, 0.27 mmol) were added into a vial equipped with a stirring bar and purged with N₂. Anisole (400 μL) was added and the open vial was placed under a stream of N₂ for ~2 min. The vial was capped and the mixture was heated to 110° C. for 32 min, at which time the reaction was found to be complete.

3A. Alternative Preparation of N¹-{3-fluoro-4-[(6-(methyloxy)-7-{[3-(4-morpholinyl)propyl]oxy}-4-quinolinyl)oxy]phenyl}-N¹-(4-fluorophenyl)-1,1-cyclopropanedicarboxamide A flask was charged with Pd(OAc)₂ (147 mg, 0.02 eq), racemic-2-(di-tert-butylphophsphinino)-1,1'-binaphyl (47 mg, 0.04 eq) and toluene (25 mL) under N₂ and the mixture was stirred at room temperature for 30 min. NMP (4 mL) and phenol (10.87 g, 1.1 eq) were added to the mixture and stirred for 5 min. K₃PO₄ (8.2 g, 1.3 eq) and Cl-quinoline (60) (10 g, 1 eq) were added sequentially under nitrogen. The reaction mixture was heated to 95° C. over about 30 min and stirred at 95° C. for 1.5 h.

Upon completion, the mixture was cooled to 60° C., whereupon 2-methylTHF (50 mL) and 20% NaHSO₃ (60 mL) were added. The mixture was stirred at 60° C. for 1 h and the layers separated. The organic solution was cooled to 50° C. and the solution decolorized with Darco G 60 (1.2 g) at 45-50° C. for 60 min. The mixture was filtered through a pad of celite and washed with a solution of 2-MethylTHF (50 mL) and MeOH (10 mL). To the solution was added Bu₃P (3.86 mL, 0.52 eq) and stirred for 30 min at room temperature. A solution of maleic acid (7.6 g, 2.2 eq) in water (60 mL) was added to the organic solution and the temperature was maintained in the range of 20-30° C. The mixture was stirred for 5 min and layers were separated. The aqueous solution was added to a slurry of 2-MethylTHF (80 mL) and Na₂CO₃ (1.64 g, 2.42 eq) and stirred for 10 min until the carbonate was dissolved. The organic solution was washed with 10% brine (50 mL) and the organic solvent removed to give 17.4 g of crude product with 97% purity (crude yield=92%). Acetonitrile (30 mL) and NMP (5 mL) were added to the crude product. The mixture was warmed to 65-70° C. and stirred for 1 h. Water (10 mL) was added slowly. The mixture was cooled to room temperature, stirred overnight, filtered, and washed with cold acetonitrile (10 mL). The product was dried in vacuo to yield 15.6 g of desired product (yield=83%) with >99% purity.

The invention claimed is:

1. A method comprising contacting a compound of formula I:

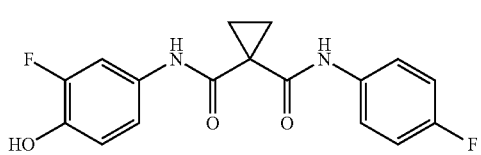

with a compound of formula II:

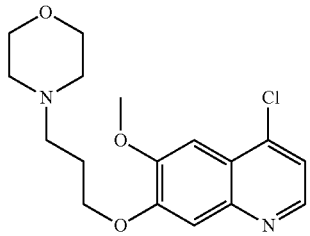

under such conditions to form a compound of formula III:

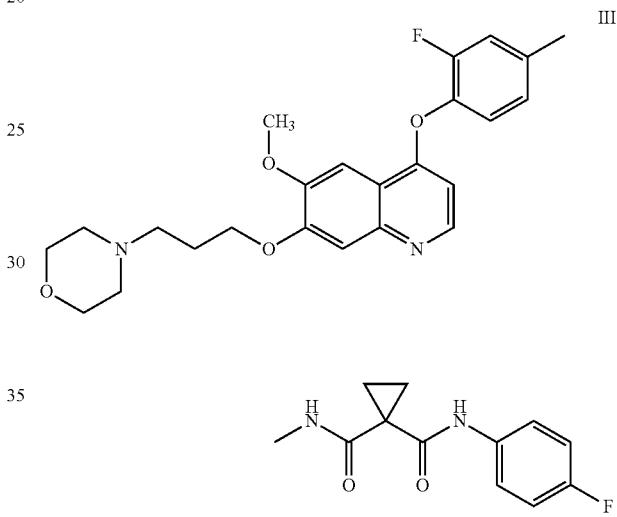

wherein the compound of formula I and compound of formula II are contacted in the presence of a base, a palladium catalyst a phosphine ligand, and a suitable solvent.

2. The method of claim 1 wherein the base is Na₂CO₃, K₂CO₃, K₃PO₄ or potassium tert-butoxide; the palladium catalyst is Pd(OAc)₂; and the ligand is 1'-(di-tert-butylphosphino)-1,2,3,4,5-pentaphenylferrocene; 1,2,3,4,5-pentaphenyl-1'-(di-tert-butylphosphino) ferrocene; 2-di-tert-butylphosphino-2'-(N,N-dimethylamino)biphenyl; di-tert-butyl(2',4',6'-triisopropylbiphenyl-2-yl)phosphine; racemic 2-[di(tert-butyl)phosphino]-1,1'-binaphthyl; 2-di-tert-butylphosphino-3,4,5,6-tetramethyl-2',4',6'-triisopropyl-1,1'-biphenyl; 2-(di-tent-butylphosphino)-1-phenylindole; N-2-methoxyphenyl-2-di-tert-butylphosphino pyrrole; 1-phenyl-2-(di-tent-butyl-phosphino)-1H-pyrrole; 2-(di-t-butylphosphino)-2'-methylbiphenyl; 2-(di-tert-butylphosphino)biphenyl; or a combination thereof; and the solvent is toluene, NMP, DMPU, anisole, a combination of toluene and NMP, or a combination of toluene and DMPU.

3. The method claim 1 wherein the phosphine ligand is racemic-2-(di-tent-butylphosphino)-1,1'-binaphthyl.

4. The method claim 1 wherein the compound of formula I is prepared by contacting under suitable conditions a compound of formula IV:

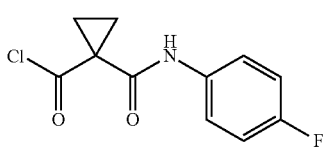

IV with a p-aminophenol of formula V:

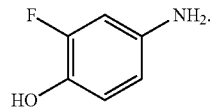

V

5. The method of claim 4 wherein the p-aminophenol is prepared by the reduction of a p-nitrophenol of formula VII:

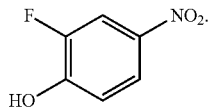

VII

6. The method of claim 5 wherein the reduction of the compound of formula VII is carried out in the presence of a Pd/C catalyst or a Pt/V catalyst.

7. A method comprising:
a) reducing 2-fluoro-4-nitrophenol to form 4-amino-2-fluorophenol;
b) contacting 1-{[(4-fluorophenyl)amino]carbonyl}cyclopropanecarbonyl chloride with 4-amino-2-fluorophenol in the presence of a base to form $N^1$-(3-fluoro-4-hydroxyphenyl)-$N^1$-(4-fluorophenyl)-1,1-cyclopropanedicarboxamide; and
c) contacting $N^1$-(3-fluoro-4-hydroxyphenyl)-$N^1$-(4-fluorophenyl)-1,1-cyclopropanedicarboxamide with a compound of formula IIa:

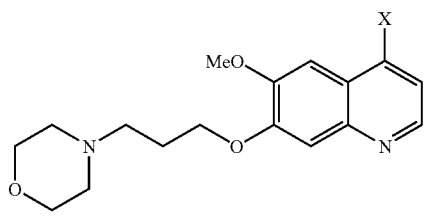

IIa under such conditions to form $N^1$-{3-fluoro-4-[(6-(methyloxy)-7-{[3-(4-morpholinyl)propyl]oxy}-4-quinolinyl)oxy]phenyl}-$N^1$-(4-fluorophenyl)-1,1-cyclopropanedicarboxamide; wherein X is a leaving group.

8. The method of claim 7 wherein in step (a) the 2-fluoro-4-nitrophenol is reduced in the presence of a Pd/C catalyst.

9. The method of claim 7 wherein in step (a) the 2-fluoro-4-nitrophenol is reduced in the presence of a Pt/V catalyst.

10. The method of claim 7 wherein in step (c) $N^1$-(3-fluoro-4-hydroxyphenyl)-$N^1$-(4-fluorophenyl)-1,1-cyclopropanedicarboxamide is contacted with the compound of formula IIa in the presence of a base and a Pd catalyst.

11. The method of claim 7 wherein X is Cl.

* * * * *